United States Patent [19]

Suchart

[11] Patent Number: 5,346,500

[45] Date of Patent: Sep. 13, 1994

[54] SUTURE CUTTING SCISSOR APPARATUS

[76] Inventor: Sood Suchart, 6036 N. 19th Ave., Suite 311, Phoenix, Ariz. 85015

[21] Appl. No.: 18,234

[22] Filed: Feb. 16, 1993

[51] Int. Cl.$^5$ .............................................. A61B 17/32
[52] U.S. Cl. ................................... 606/138; 606/174
[58] Field of Search ......... 606/138, 167, 174, 205–211

[56] References Cited

U.S. PATENT DOCUMENTS 3,443,313  5/1969  Profy ..................................... 606/138
4,271,838  6/1981  Lasner et al. ........................ 606/138

Primary Examiner—Stephen C. Pellegrino
Assistant Examiner—William W. Lewis
Attorney, Agent, or Firm—H. Gordon Shields

[57] ABSTRACT

Suture cutting apparatus includes a notched holding blade having a predetermined thickness and a cutting blade for cutting suture elements held in the notch of the holding blade. The notch of the holding blade is generally axially extending with respect to the longitudinal axis of the holding blade and the notch extends inwardly from an outer tip of the holding blade. The holding blade is of a predetermined thickness so that the bottom of the blade may be disposed on a knot and the cutter blade will cut off the suture elements disposed in the notch at a predetermined distance above the knot. The predetermined distance is the thickness of the holding blade.

17 Claims, 2 Drawing Sheets

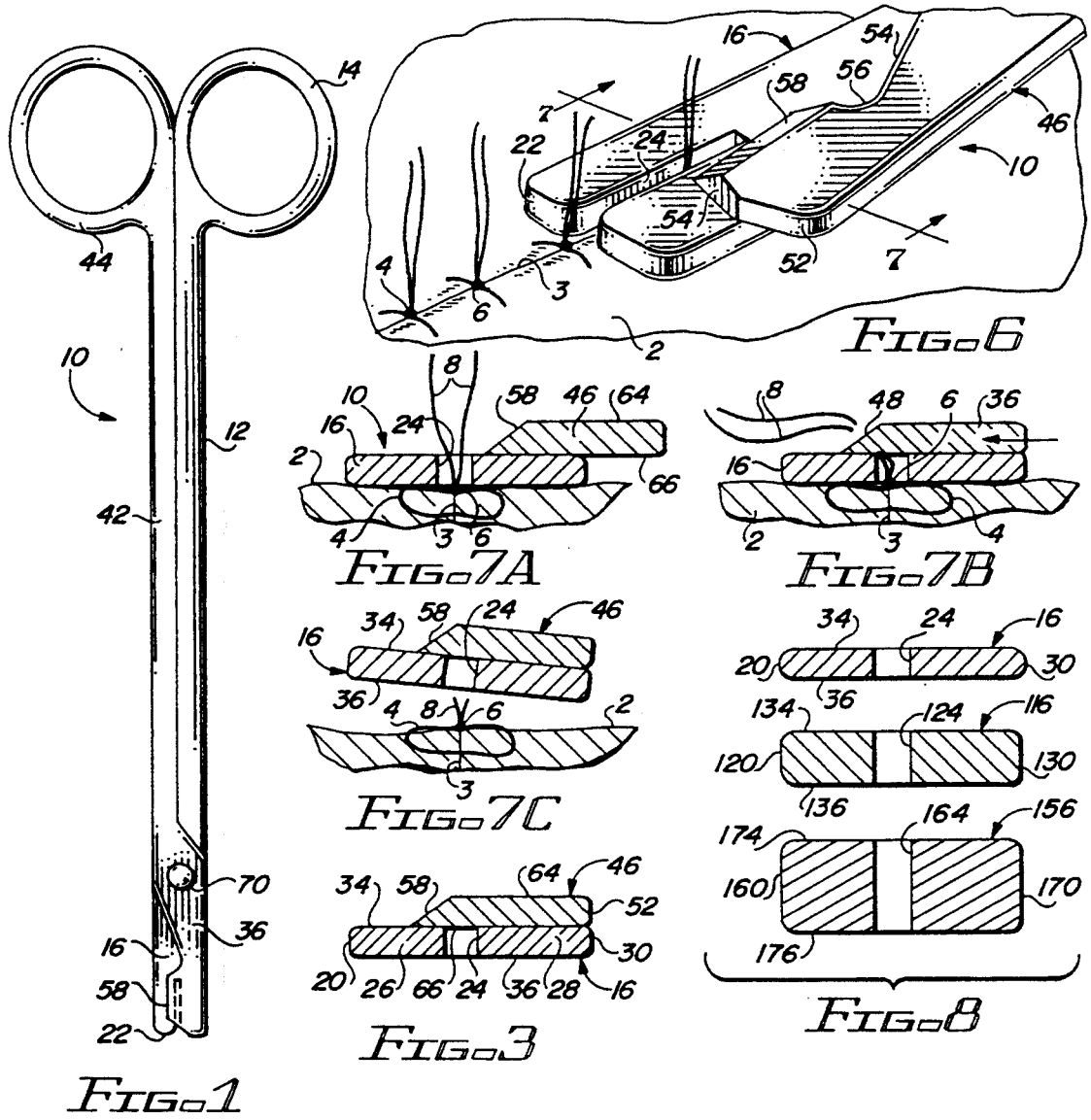

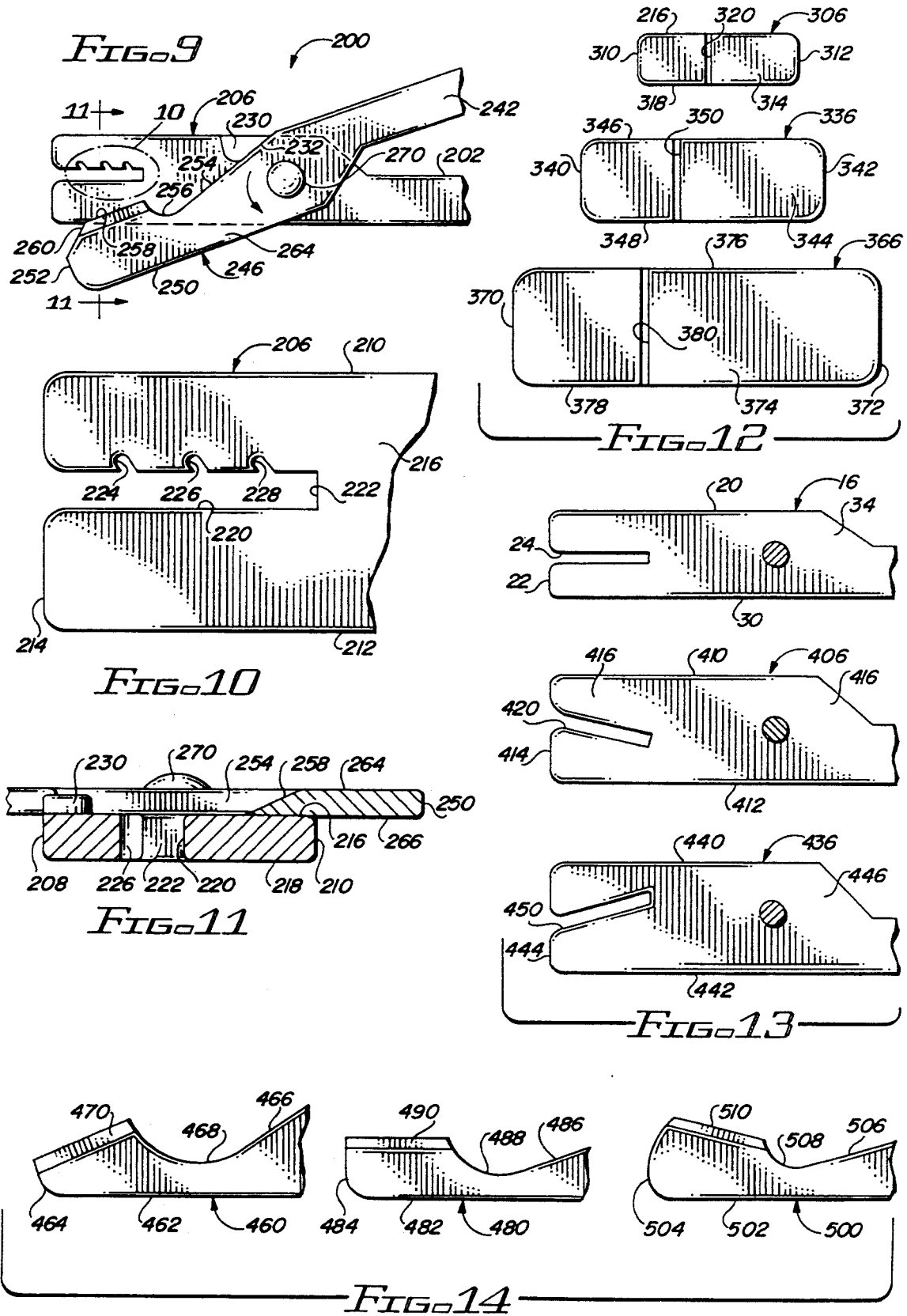

SUTURE CUTTING SCISSOR APPARATUS

BACKGROUND OF THE INVENTION

1. Field of the Invention

This invention relates to scissors and, more particularly, to scissors for cutting sutures a predetermined distance above a knot.

2. Description of the Prior Art

In different types of surgical procedures, it is advantageous to have the sutures cut a predetermined distance above the knots. The predetermined distance varies, depending on the type of surgical procedure involved. For example, in plastic surgery, where there may be numerous fine sutures, a surgeon may prefer to have the sutures cut about two millimeters above the knot. In other types of surgery, a surgeon may prefer to have the sutures cut about four millimeters above a knot. In still other types of surgery, where the presence of the suture is not a particular problem, a surgeon may prefer to have the sutures cut about eight millimeters above the knot, or above the skin.

At the present time, there are no scissors available that will cut a suture consistently the same distance above a knot. Rather, the sutures are simply snipped or cut after "eyeballing" the length of the suture above the knot or skin.

While there have been different types of scissors in the prior art which include a slot or similar element for holding an element to be cut, or for snipping an element to be cut in a particular manner, the problem of cutting sutures a predetermined distance above a knot has not been addressed, in so far as is known. Moreover, the slots or receiving elements haven't been aligned with the longitudinal axis of the scissors blade for ease of aligning the scissors with sutures to be cut and for maximum visibility. With respect to the latter point, the knots and sutures are always readily visible in the apparatus of the present invention, and they are held generally perpendicularly to the cutting blade element. None of these features are found in the prior art. Accordingly, the apparatus of the present invention addresses and solves the problems of holding sutures and of consistently the cutting sutures a predetermined distance above their knots.

U.S. Pat. No. 257,982 (Schmidt) discloses snipping scissors at the front end of nippers designed to open bottles. The apparatus includes a squeezing element for removing corks from bottles, as from champagne bottles, and nipping scissors are located in the front of the apparatus for cutting wire and twine.

U.S. Pat. No. 576,050 (Ford) discloses shears in a combination tool. The shears include notches that cooperate with blades. The notches hold cords to be cut. The tool is a combination tool, and the combination includes a hammer, a screw driver, as well as scissors.

U.S. Pat. No. 1,274,669 (Bohn) discloses a surgical instrument designed for cutting portions of bone cartilage, etc., within the nose. The apparatus includes a tube, and cutter elements extend through the tube, and outwardly from the tube, for cutting.

U.S. Pat. No. 2,038,916 (Vorwerk) discloses bag opening scissors which include teeth elements designed to lift stitches of a bag and to hold the stitches while a blade cuts them. The teeth elements extend perpendicularly to the longitudinal axis of a scissor blade and they are aligned with the scissor blade so that stitches being held by the teeth are cut when the opposite blade of the scissor contacts them.

U.S. Pat. No. 2,103,597 (Ravenscroft) discloses a cable cutter apparatus. The cable cutter apparatus includes a notch for holding a cable cut by a blade element.

U.S. Pat. No. 2,374,795 (Williams) discloses scissors apparatus with a notched extension. The apparatus comprises two separate elements combined into one apparatus, but there is no cooperation between the two elements. The extension does not hold elements to be cut by the scissors.

U.S. Pat. No. 4,753,009 (Haga) discloses a multi-function sewing implement that includes a scissor portion and a notched extension element. There is a cutting blade on the notched extension element, but there is no cooperation between the scissors element and the notched extension.

The apparatus of the present invention includes a notch on one blade of a scissors for receiving and holding sutures to be cut by a cutting blade. The notched blade has a predetermined thickness so that the bottom of the blade may be disposed on a knot, and the cutting blade will then cut the sutures above the knot a predetermined distance in accordance with the thickness of the holding blade.

SUMMARY OF THE INVENTION

The invention described and claimed herein comprises suture cutting scissor apparatus that includes a holding blade and a cutting blade. The holding blade is of a predetermined thickness and it includes a notch for receiving and holding the sutures. The sutures extend into the notch and the bottom of the holding blade is placed on the knot and the cutting blade then cuts the sutures at the predetermined distance above the knot, which predetermined distance is equal to the thickness of the suture holding blade.

Among the object of the present invention are the following:

To provide new and useful scissors apparatus;

To provide new and useful scissor apparatus for cutting sutures;

To provide new and useful scissor apparatus having a holding blade and a cutting blade;

To provide new and useful scissor apparatus having a notched holding blade of a predetermined thickness and a cutting blade for cutting elements held in the notch of the holding blade; and To provide new and useful suture cutting apparatus having a notched holding blade of a predetermined thickness for holding sutures a predetermined distance above a knot and a cutting blade for cutting the held sutures.

BRIEF DESCRIPTION OF THE DRAWING

FIG. 1 is a top view of the apparatus of the present invention.

FIG. 2 is an enlarged view of a portion of the apparatus of FIG. 1.

FIG. 3 is a view in partial section taken generally along line 3—3 of FIG. 2.

FIG. 4 is a top view of a portion of the apparatus of the present invention.

FIG. 5 is a top view of another portion of the apparatus of the present invention.

FIG. 6 is a perspective view illustrating the apparatus of the present invention in its use environment.

FIGS. 7A, 7B, and 7C are sequential views illustrating the operation of the apparatus of the present invention and taken generally along line 7—7 of FIG. 6.

FIG. 8 is a view in partial section illustrating three embodiments of a portion of the apparatus of the present invention.

FIG. 9 is a top view of a portion of an alternate embodiment of the apparatus of the present invention.

FIG. 10 is an enlarged top view of a portion of the apparatus of FIG. 9 taken generally from oval 10 of FIG. 9.

FIG. 11 is a view in partial section taken generally along line 11—11 of FIG. 9.

FIG. 12 is an end view illustrating portions of three different embodiments of a portion of the apparatus of the present invention.

FIG. 13 is a top view illustrating portions of additional embodiments of the apparatus of the present invention.

FIG. 14 is a top view of portions of three additional embodiments of the apparatus of the present invention.

DESCRIPTION OF THE PREFERRED EMBODIMENT

FIG. 1 is a top view of suture cutting scissor apparatus 10 of the present invention. The scissors 10 include a handle element 12 with a ring 14 at one end and a bottom holder blade 16 at the opposite end. The scissor apparatus 10 also includes a second handle element 42 with a ring 44 at one end and an upper cutter blade 46 at the opposite end. The two handle elements 12 and 42 are secured together by a pivot pin 70. By holding the scissors 10 by the rings 14 and 44, the handle elements 12 and 42 and the blade elements 16 and 46 are moved relative to each other.

The blade elements, including the holder blade 16 and the cutter blade 46 are of particular importance. The blades 16 and 46 are shown in detail in FIGS. 2, 3, 4, and 5. For the following discussion, reference will primarily be made to FIGS. 2, 3, 4, and 5.

In FIG. 2, the two blade elements 16 and 46 are shown disposed adjacent to each other and in an overlying relationship. The overlying relationship is further illustrated in FIG. 3, which comprises a view in partial section taken generally along 3—3 of FIG. 2 through the blade element 16 and 46. FIGS. 4 and 5 are top views of the holder blade 16 and the cutter blade 46 respectively.

It will be noted, by reference to FIG. 1, that the overall length of the scissor apparatus 10 from the pivot pin 70 shows a relatively high ratio between the length of the cutter blades 16 and 46 from the pivot pin 70 and the handle elements 12 and 42 and their respective ring elements 14 and 44. That is, the length of the blade elements 16 and 46 from the pivot pin 70 is relatively short as compared to the length of the handle elements 12 and 42 and their rings 14 and 44, respectively from the pivot pin 70. By reference to FIGS. 2, 3, 4, and 5, the configuration of the blade elements is shown in detail. While the blade elements are relative short, they are of a particular configuration in accordance with their particular use purpose of cutting suture elements.

As shown in FIG. 4, the holder element 16 is of a generally rectangular configuration outwardly from a pivot aperture 18. This is an outer side 20 which extends to a tip 22. The side 20 is generally straight. The side 20 extends to an outer tip 22. Generally parallel to the side 20 is a side 30. The blade 16 includes a top surface 34 and a bottom surface 36, and a pair of side surfaces 28 and 30. The top and bottom surfaces 34 and 36 are generally planar in configuration and are generally parallel to each other. The side surfaces 20 and 30 are similarly generally parallel to each other. The corners, or the junctures of adjacent sides, are preferably rounded.

Extending inwardly from the outer end or tip 22 is a longitudinally extending slot 24. The slot 24 is generally parallel to the side surfaces 20 and 30 and extends fully between the top and bottom surfaces 34 and 36, respectively. The purpose of the slot 24 is to receive suture elements to be cut, as will be discussed below in conjunction with FIGS. 7A, 7B, and 7C.

The slot 24 divides the outer portion of the cutter blade 16 into two portions, a portion 26 and a portion 28. The two portions 26 and 28 need not be of equal size. That is, the slot 24 need not bisect the tip portion of the blade 16. However, the slot 24 is generally parallel to the sides 20 and 30 and is generally aligned with the longitudinal axis of the holder blade 16 and the handle 12.

The cutter blade 46 is of a generally irregular configuration outwardly from a pivot aperture 48. The cutter blade 46 includes a generally straight outer side 50 which extends to a distal tip 52. The side 50 extends generally from the area of the pivot aperture 48.

The side opposite the side 50 is of a generally irregular configuration. From the area of the pivot aperture 48, there is an inwardly sloping side portion 54 which extends to a concave portion 56. The concave portion 56 curves outwardly from the inwardly sloping side portion 54 and terminates in a cutting edge 58. The cutting edge 58 is generally parallel to the outer side 50.

Between the cutting edge 58 and the tip 52 there is a outwardly sloping side portion 60. The cutting edge 58 extends generally outwardly from a front shank portion 62 of the cutter blade 46. The front shank portion may be defined as the front portion of the cutter blade between the tip 52, the side 50, the sloping side 60, and the side or recess 56.

When the two handle elements 12 and 42 are secured together, the handle element 42 is disposed on top of the handle element 12 with the pivot apertures 18 and 48 aligned and the pivot pin 70 extends through the aligned apertures 18 and 48 to secure the two handle elements, and their respective blades, together.

When the handle elements 12 and 42 are disposed adjacent to each other, with the rings 14 and 44 also disposed against each other, as illustrated in FIG. 1, the cutting edge 58 is disposed on the tip portion 26, just past the slot 24.

Referring to FIGS. 6, 7A, 7B, and 7C, as well as to FIG. 1, the scissor apparatus 10 of the present invention is illustrated in its use environment. In FIG. 6 and in FIG. 7A, 7B, and 7C, there is shown skin 2 with an incision 3. A plurality of sutures 4 are shown along the incision 3. Each suture includes a knot 6 with loose ends 8 extending upwardly from the knot 6.

The bottom surface 36 of the holder blade 16 is disposed on the surface of the skin 2 with the knot 6 and the end 8 of the suture 4 disposed in the slot 24, the ends 8 are ready to be cut. It will noted that the width of the slot 24 is sufficient to fully receive the knots 6.

With the ends 8 of the suture 4 disposed in the slot 24, the cutter blade 46 is moved relative to the holder blade 16. The cutting edge 58 is then moved relative to the holder blade 16. As the cutter blade 58 moves across the slot 24, the ends 8 of the suture 4 are cut. The ends 8 are cut a predetermined distance of the skin surface. Above the surface of the skin 2 in accordance with the thickness of the holder blade 16, or in accordance with the distance between the top surface 34 and the bottom surface 36 of the holder blade 16.

Referring specifically to FIG. 6, it will be seen that each of the sutures 4 may be cut consecutively by the scissors apparatus 10 as the holder blade 16 is moved generally along the incision 8. With the bottom 36 of the holder blade 16 disposed on the surface of the skin 2, the suture ends 8 will be of uniform height when the sutures all have been cut.

The movement of the scissors apparatus 10 is accomplished by a surgeon moving the holder blade 16, and accordingly the handle element 12, generally along the skin 2 so that the sutures are conveniently moved into the slot 24. Again, as shown in FIG. 6, the holder blade 16, and its handle element 12, are preferably aligned with the incision 3 so that the sutures 4 may be cut conveniently and consecutively as the scissors apparatus 10 is moved axially along the incision 3.

From reference to FIG. 2, it will be noted that the cutting edge 58 is generally the same length as the slot 24. Depending on the length of the slot 24 and the density of or distance between the sutures, it will be noted that more than one suture may be cut at a time.

It will also be understood that as the surgeons fingers extend through the rings 14 and 24, the scissors may be easily grasped, moved, and used. The ring 14 will generally receive a users thumb, and will generally be held in a fixed orientation with respect to the skin 2 in with respect to the incision 3 and the sutures 4. The ring 44 will receive a finger, either an index finger or a middle finger, and the handle element 42 will be move relative to the handle element 12 to move the cutter blade 46 relative to the holder blade 16.

It will be understood that maximum visibility is provided by the apparatus of the present invention. That is, regardless of how small are the sutures 4, with the slot 24 extending generally axially with respect to the longitudinal axis of the holder blade 16 and of the handle element 12, and the cutter blade 46 with its handle element 42 always moving so that the cutting edge 58 is generally pivoting from the side, there is maximum visibility at all times of the incision 3 and the sutures 4.

In FIG. 8, three different holder blades, including the holder blade 16, and a holder blade 116 and a holder blade 156, are shown. The holder blades 16, 116, and 156 differ from each other only in the thickness or in the difference between their top surfaces and bottom surfaces. The holder blade 16 is the thinnest of the three, with a distance between its top surface 34 and bottom surface 36 the least distance of the three.

The cutter blade apparatus 116 includes a pair of side edges 120 and 130, a top surface 134 and a bottom surface 136. The distance between the top surface 134 and the bottom surface 136 is greater than the distance between the top surface 34 and the bottom surface 36. However, the distance between the side 120 and the side 130 is substantially the same as the distance between the sides 20 and 30 of the holder blade 16.

The holder blade 156 includes a pair of sides 160 and 170 and a top surface 174 and a bottom surface 176. A slot 164 extends between the top and bottom surfaces 174 and 176, as does the slot 24 of the holder blade 16 and the slot 124 for the holder blade 116.

The distance between the top surface 174 and the bottom surface 176 is greater than the distance between the top surface 134 and the bottom surface 136 of the holder blade 116. However, and again, the distance between the sides 160 and 170 is substantially the same as the distance between the side 120 and 130 between and the sides 20 and 30 of the holder blades 116 and 16, respectively. Again, the only differences among the holder blade 156, the holder blade 116, and the holder blade 16, is the height or thickness of the holder blades, or the distance between the top surface and bottom surfaces.

It will be understood that with the bottom surfaces 36, 136, and 176, placed on the skin, and with a knot and suture ends extending into the respective slots, a cutting blade disposed on the top surfaces will leave a predetermined length of suture ends remaining after being cut, and the suture ends will be of different lengths, depending on which holder blade 16, 116, or 156, is used. With the holder blade 156, the suture ends will be longer than with either of the holder blades 116 or 16.

With the apparatus of the present invention, a surgeon may determine the length of the suture ends that is desired. As discussed above, typically the desired suture ends may be two millimeters, four millimeters, or six millimeters. Accordingly, the thickness of the cutter blades 16, 116, and 156 may typically be two millimeters, four millimeters, or six millimeters, respectively.

Regardless of the thickness of the holder blade, the thickness of the cutter blade will remain substantially the same. There is no reason for the thickness of the cutter blade, or the design of the cutter blade, to vary merely because of the a varying thickness of a holder blade.

The above discussion assumes a surgeon using a scissor apparatus 10 is right handed. If a surgeon is left handed, the surgeon's left thumb would extend through the ring 44 and the surgeon's index finger or middle would extend through the ring 14. Moreover, it is obvious that the pivoting may be in the opposite direction from that illustrated herein. The holder elements and cutter elements accordingly may be mirror images of the embodiment shown. In other words, it is irrelevant as to the direction of pivoting of the cutter blade relative to the holder blade.

FIG. 9 is a top view of a portion of scissor apparatus 200 which comprises an alternate embodiment of the scissors apparatus 10 discussed above. In FIG. 9 are shown portions of two handle elements 202 and 242 secured together by a pin 270. The outer or distal portions of the handle element 202 and the handle element 242 comprise a holder blade 206 and a cutter blade 246, respectively.

FIG. 10 is an enlarged view of a portion of the holder blade 206 illustrating the configuration of the holder blade 206. FIG. 11 is a view in partial section through the holder blade 206 and the cutter 246. FIG. 11 is taken generally along line 11—11 of FIG. 9. For the following discussion of the scissor apparatus 200, reference will be made to FIGS. 9, 10, and 11.

The scissor apparatus 200 comprises the handle element 202 secured to the holder blade 206. The holder blade 206 includes a side 210 and a side 212. The sides 210 and 212 are generally parallel to each other. The holder blade 206 terminates remote from the handle element 202 in an end 214. The end 214 is generally perpendicular to the sides 210 and 212. The corners or junctures of the sides 210 and 212 with the end 214 are appropriately radiused and are accordingly void of sharp edges.

The holder blade 206 includes a top surface 216 and a bottom surface 218. The surfaces 216 and 218 are generally flat or planar and are generally perpendicular to each other. The juncture of the surfaces 216 and 218 with the sides 210 and 212 and with the end 214 are appropriately radiused or curved to prevent sharp edges which could inadvertently cause problems or harm to a patient, etc.

A suture receiving slot 220 extends inwardly from the end 214 into the holder blade 206. The slot 220 is generally parallel to the sides 210 and 212. The slot 220 terminates in an end 222 remote from the end 214 of the holder blade 206.

On one side of the slot 220, remote from the cutter blade 246, are three notches 224, 226, and 228. The notches 224, 226, and 228 extend at an diagonal angle upwardly or outwardly towards the tip 214 and the edge 210 relative to the slot 220. The purpose of the notches or serrations 224, 226, and 228 is for catching a suture or preventing a suture from slipping out of the notch 220, and accordingly the notches insure that the sutures remain in the slot 220 as the cutter blade 246 is moved to cut the sutures.

Extending upwardly from the top surface 216 of the holder blade 206 and adjacent to the side 210 is a stop element 230. The stop element is of a generally terse teardrop configuration with a diagonal side 232 disposed adjacent to the cutter blade 246. The purpose of the stop element 230 is to limit the opening ability of the scissor apparatus 200. That is, the stop element 230 is located on the holder blade 206 adjacent to the fastener element 270 so as to limit the movement of the cutter blade 246 with respect to the holder blade 206. The cutter blade 246 remains disposed on top of the holder bale 206.

The cutter blade 246 includes an outer side 250 and an outer tip 252. The tip 252 is shown generally perpendicularly to the side 250.

The cutter blade 246 also includes an inner sloping side 254 extending from the handle element 242 inwardly to a concave recess 256. Adjacent to the concave recess 256 is a cutting edge 258. A sloping side 260 extends between the tip and the cutting edge 258.

Cutter blade 246 also includes a top surface 264 and a bottom surface 266. The surfaces 264 and 266 are substantially parallel to each other and, as with the junctures of the various sides and surfaces of the holder blade 206, the junctures of the various sides and surfaces of the cutter blade 246 are similarly rounded or radiused for convenience and safety. Accordingly, only the cutting edge 256 provides a sharp edge at which a cutting action may take place.

As shown in FIG. 9, the inner sloping side 254 of the cutter blade 246 is disposed against the side 232 of the stop element 230. The cutter blade 246 accordingly cannot move outwardly or away from the holder blade 206 due to the abutting relationship between the stop element 230 and the inner sloping side 254 of the cutter blade 246. It will noted also that the cutting edge 258 remains disposed on the holder blade 206. Thus, the stop element 230 essentially insures that the cutting edge 258 remains disposed on top of the holder blade 206. This is primarily a safety feature to prevent inadvertent accidents with respect to the cutting edge 258 and a patient, etc.

For example, if it were desired that the scissors apparatus 200 be inverted so that the cutter blade 246 is disposed against a patients skin, the limitation of the cutting edge 258 always remaining disposed on or adjacent to the holder blade 206 would insure that the patients skin would not be inadvertently cut. Moreover, only elements disposed within the slot 220 would be cut by the cutting edge 258.

In FIG. 12, three different holder blade elements are illustrated. The three holder blades, the holder blade 306, a holder blade 336, and a holder 366, comprise three different sizes of holder blades. The three sizes vary in width, in thickness, and in the width of their respective slots which receive sutures.

The holder blade 306 is the smallest of the three holder blades. The holder blade 306 includes a pair of sides 310 and 312 and an end 314. The holder blade 306 also includes a top surface 316 and a bottom surface 318. The surfaces 316 and 318 are generally parallel to each other, as are the sides 310 and 312. A slot 320 is shown extending into the holder blade 306 from the end 314.

The holder blade 336 includes a pair of sides 340 and 342 and an end 344. The holder blade 336 also includes a top surface 346 and a bottom surface 348. The surfaces 346 and 348 are generally parallel to each other, as are the sides 340 and 342. A slot 350 extends inwardly from the end 344. The holder blade 336 is larger than the holder blade 306 in both thickness and width, or in the distance between the top surface 346 and the bottom surface 348 and between the sides 340 and 342. Similarly, the slot 350 of the holder blade 336 is wider than the slot 320 of the holder blade 306.

The holder blade 366 includes a pair of sides 370 and 372 and an end 374. The holder blade 366 also includes a top surface 376 and a bottom surface 378. The surfaces 373 and 378 are generally parallel to each other, as are the sides 370 and 372. A slot 380 extends inwardly into the holder blade 366 from the end 374.

The holder blade 366 is the largest of the three holder blades, having a greater thickness, or distance between the surfaces 376 and 378, and a greater width, or the distance between the sides 370 and 372, than either the holder blade 306 or the holder blade 366.

While the overall dimensions of the three holder blades 306, 336, and 366 differ from each other, it will be noted that the width of the slot 320, 350, and 380 also varies. This is so, of course, since the size of the sutures will generally also vary, and it is desired that the sutures be cut at different distances from the knot or from the patients skin. The smallest holder blade 306 is accordingly designed to hold the thinnest or smallest sutures closest to a knot, and the holder blade 366 is designed to hold the thickest or largest sutures farthest from a knot.

The relative dimensions of the cutter blades may be sized according to the dimensions of the holder blades. The cutting edges of the cutter blades will preferably have the same thickness, but the widths may vary according to the various widths and thicknesses of the holder blades.

FIG. 13 illustrates different angular orientations of the suture receiving slots in the holder blades. Top views of holder blades are illustrated in FIG. 13.

A holder blade 406 includes a pair of sides 410 and 412 which are generally parallel to each other. An end 414 extends between the sides 410 and 412. The holder blade 406 also includes a top surface 416.

A slot 420 is shown extending into the holder blade 406 from the end 414. The slot 420 extends diagonally from the end 414 rearwardly and into the holder blade 406 generally towards the side 412.

A holder blade 436 is also shown in FIG. 13, with a diagonal slot 450 extending in the opposite direction from the diagonal slot 420. The holder blade 436 includes a pair of generally parallel sides 440 and 442 and an end 444. The holder blade 446 also includes a top surface 446. The slot 450, a diagonal slot, extends rearwardly or into the holder blade 436 from the end 444 and generally towards the side 440. The slot 450 accordingly extends diagonally into the holder blade 436 in a generally opposite direction from the diagonal slot 420 of the holder blade 406.

The angular orientations, or the diagonal directions of the slots 420 and 450 are shown in comparison to the generally axially extending slot 24 of the holder blade 16. The slot 24 extends into the holder blade 16 generally parallel to the sides 20 and 30 from the end 22. See also FIG. 4.

In FIG. 14, three different configurations of cutter blades, or specifically configurations of cutting edges of cutter blades, are illustrated. Three cutter blades 460, 480, and 500 are shown, each with a different configuration or orientation of a cutting edge.

The cutter blade 460 includes an outer side 462 and a tip 464. The tip 464 extends generally outwardly and away from the side 462. The cutter blade 460 also includes an inner sloping side 466 which extends to a concave recess 468. A cutting edge 470 extends diagonally from the concave recess 468 to the tip 464. The tip 464 comprises an outer end of the cutter blade 460, and the cutting edge 470 extends diagonally between the tip or outer edge 464 and the portion of the concave recess 468 remote from the inner sloping side 466.

The cutter blade 480 includes an outer side 482 and a tip or outer end 484. The tip or outer end 484 is generally perpendicular to the outer side 482. The juncture of the side 482 and the end 484 is appropriately radiused or curved.

The cutter blade 480 also includes an inner sloping side 486 and a concave recess 488. A cutting edge 490 extends between the recess 488 and the end 484. The cutting edge 490 is generally straight or parallel to the side 482. The edge 490, parallel to the side 482, is also generally perpendicular to the end or tip 484.

The cutter blade 500 includes an outer side 502 and a rounded tip or end 504. The rounded tip or end 504 has a generally convex configuration.

The cutter blade 500 also includes an inner sloping side 506 which extends to a concave recess 508. A cutting edge 510 extends diagonally from the concave recess 508 outwardly toward the convexly curved or rounded end 504. The cutting edge 510 is generally diagonally extending, but in the opposite direction from the cutting edge 470 of the cutter blade 460. Thus, in the cutter blade 500, the maximum width of the cutter blade is at the outer tip or end 504, while the cutting edge 510 slopes inwardly from the outer end 504 to the concave recess 508. The concave recess 508 is of a minimum radius in the cutter blade 500. In the configuration of the cutter blade 460, the concave recess 468 is of maximum radius between the side 466 and the cutting edge 470.

It will be understood that the particular configuration of a cutter blade will be appropriately matched with the configuration of a holder blade with respect to the configurations of the cutting edges and the suture receiving slots. Under some circumstances, a particular configuration of a holding slot and of a cutting edge may be more effective in cutting certain sutures than another configuration. Moreover, as discussed above, the widths of the holder blades and the thickness of the holder blades may vary, depending on the particular sutures being cut and the desired distance above a knot that is desired that the sutures be cut.

Finally, it will be understood that the widths of the holder slots may also vary, depending on the types of sutures to be cut, etc.

While the descriptions above for the apparatus of the present invention are all related to the cutting of sutures, it is obvious that the apparatus may also be used in a general household environment, as for cutting threads, or the like. There is often a need for cutting threads at a desired distance above a knot or above cloth, and the cutter apparatus of the present invention is ideal for such use. Not only are the scissor apparatus embodiments of the present invention safe to use, they are also maximum in efficiency in holding and cutting sutures or threads at a desired, predetermined, height above a knot, or the like.

What I claim is:

1. Scissor apparatus for holding and cutting sutures extending outwardly from a sutured skin surface, comprising, in combination:
   holder blade means, including
      a holder blade having a planar bottom surface to be disposed on the sutured skin surface and a planar top surface parallel to the planar bottom surface,
      holder handle means secured to the holder blade for positioning the holder blade relative to sutures to be cut,
      a slot in the holder blade for receiving sutures to be cut, and
   notch means in the slot for receiving sutures to be cut; and
   cutter blade means pivotally secured to the holder blade means, including
      a cutter blade for cutting the sutures received in the slot of the holder blade means, and
      cutter handle means secured to the cutter blade for moving the cutter blade relative to the holder blade to cut the sutures in the slot of the cutter blade.

2. The apparatus of claim 1 in which the holder handle means and the cutter handle means each include a ring for receiving fingers of a user for positioning the holder blade means and for moving the cutter blade means relative to the holder blade means.

3. The apparatus of claim 1 in which the bottom surface of the holder blade is spaced apart from the top surface a predetermined distance in accordance with a desired length of suture remaining after being cut.

4. The apparatus of claim 1 in which the holder blade means has a first length and the holder handle means has a second length which is substantially greater than the first length.

5. The apparatus of claim 1 in which the holder blade means further includes a stop element to limit the relative movement between the holder blade and the cutter blade means.

6. The apparatus of claim 1 in which the holder blade means further includes an end remote from the holder handle means, and the slot extends into the holder blade from the end.

7. The apparatus of claim 6 in which the slot extends generally perpendicularly to the end.

8. The apparatus of claim 6 in which the slot extends diagonally relative to the end.

9. Scissor apparatus for cutting sutures adjacent to sutured skin, comprising in combination,
- holder blade means, including
  - a holder blade having a planar bottom surface to be disposed on the sutured skin,
  - a slot in the holder blade for receiving a suture and its knot to be cut,
  - a planar top surface spaced apart from and parallel to the bottom surface a predetermined distance in accordance with a desired length of suture remaining after being cut,
  - at least a single notch in the slot for holding sutures to be cut, and
  - holder handle means secured to the holder blade for positioning the holder blade and the slot relative to the suture to be cut; and
- cutter blade means pivotally secured to the holder blade means, including
  - a cutter blade for cutting the suture disposed in the slot of the holder blade, and
  - cutter handle means secured to the cutter blade for moving the cutter blade to cut the suture.

10. The apparatus of claim 9 in which the cutter blade is disposed adjacent to the top surface of the holder blade.

11. The apparatus of claim 9 in which the slot in the holder blade is generally aligned with the holder handle means.

12. The apparatus of claim 9 in which the cutter blade means includes a shank portion, and the cutter blade extends outwardly from the shank portion.

13. The apparatus of claim 9 in which the holder blade means includes a distal tip remote form the holder handle means, and the slot extends from the distal tip towards the holder handle means.

14. The apparatus of claim 9 in which the slot has a predetermined width for receiving a suture knot.

15. The apparatus of claim 9 in which the holder blade means further includes a outer tip, and the slot extends into the holder blade from the outer tip.

16. The apparatus of claim 15 in which the slot of the holder blade means extends generally perpendicularly to the outer tip.

17. The apparatus of claim 15 in which the slot of the holder blade means extends in a diagonal direction relative to the outer tip.

* * * * *